US006855159B1

(12) United States Patent
Tanner et al.

(10) Patent No.: US 6,855,159 B1
(45) Date of Patent: Feb. 15, 2005

(54) SURGICAL GUIDE LINE ASSEMBLY AND SEPARATOR ASSEMBLY FOR USE DURING A SURGICAL PROCEDURE

(75) Inventors: Howard M. Tanner, Logan, UT (US); Hugh H. Trout, Chevy Chase, DC (US)

(73) Assignee: Eva Corporation, Bethesda, MD (US)

( * ) Notice: Subject to any disclaimer, the term of this patent is extended or adjusted under 35 U.S.C. 154(b) by 0 days.

(21) Appl. No.: 09/936,202

(22) PCT Filed: Feb. 4, 2000

(86) PCT No.: PCT/US00/03871

§ 371 (c)(1),
(2), (4) Date: Apr. 1, 2002

(87) PCT Pub. No.: WO00/45710

PCT Pub. Date: Aug. 10, 2000

Related U.S. Application Data
(60) Provisional application No. 60/118,779, filed on Feb. 5, 1999, and provisional application No. 60/137,702, filed on Jun. 7, 1999.

(51) Int. Cl.[7] .................................................. A61F 2/06
(52) U.S. Cl. ...................... 623/1.11; 623/1.1; 606/108; 606/224
(58) Field of Search ................................ 623/1.1, 1.11, 623/11.11, 902, 903, 1.13, 1.23, 29, 2.41, 23.26; 606/1, 108, 198, 191, 222–233, 53, 72, 99, 139–150

(56) References Cited

U.S. PATENT DOCUMENTS

| | | | | |
|---|---|---|---|---|
| 3,902,198 A | * | 9/1975 | Cooper | 623/8 |
| 4,290,877 A | * | 9/1981 | Blickensderfer | 204/298.27 |
| 4,323,071 A | * | 4/1982 | Simpson et al. | 606/194 |
| 4,586,923 A | * | 5/1986 | Gould et al. | 604/95.04 |
| 4,619,641 A | * | 10/1986 | Schanzer | 604/8 |
| 5,002,488 A | * | 3/1991 | Homsy | 433/169 |
| 5,358,498 A | * | 10/1994 | Shave | 606/224 |
| 5,360,341 A | * | 11/1994 | Abramowitz | 433/215 |
| 5,391,172 A | * | 2/1995 | Williams et al. | 623/1.11 |
| 5,447,512 A | * | 9/1995 | Wilson et al. | 606/139 |
| 5,454,820 A | * | 10/1995 | Kammerer et al. | 606/148 |
| 5,607,477 A | * | 3/1997 | Schindler et al. | 623/23.72 |
| 5,810,745 A | * | 9/1998 | Chaffringeon | 600/581 |
| 5,944,730 A | * | 8/1999 | Nobles et al. | 606/151 |
| 6,024,764 A | * | 2/2000 | Schroeppel | 606/198 |
| 6,033,412 A | * | 3/2000 | Losken et al. | 606/105 |
| 6,039,755 A | * | 3/2000 | Edwin et al. | 623/1.15 |
| 6,102,918 A | * | 8/2000 | Kerr | 606/108 |
| 6,258,083 B1 | * | 7/2001 | Daniel et al. | 606/15 |
| 6,270,516 B1 | * | 8/2001 | Tanner et al. | 606/213 |
| 6,312,421 B1 | * | 11/2001 | Boock | 604/509 |
| 6,389,313 B1 | * | 5/2002 | Marchitto et al. | 604/21 |

OTHER PUBLICATIONS

Chemical Registry Listing for Gore–Tex Nov. 18, 2003.*

* cited by examiner

*Primary Examiner*—Glenn K. Dawson
(74) *Attorney, Agent, or Firm*—Collier Shannon Scott, PLLC

(57) ABSTRACT

The present invention is directed to a surgical guide line assembly (10) for use during a surgical procedure. The surgical guide assembly (10) permits the manipulation of a surgical component with a vessel during a surgical procedure, such as for example an intravascular procedure. The surgical guide line assembly (10) includes a guide line component (11) having a proximal end and a distal end, and at least one suture (12) secured to the distal end of the guide line component (11). The present invention is also directed to a surgical separator assembly (60) for use in separating at least two surgical components during a surgical procedure in a vessel.

15 Claims, 8 Drawing Sheets

SURGICAL GUIDE LINE ASSEMBLY AND SEPARATOR ASSEMBLY FOR USE DURING A SURGICAL PROCEDURE

CROSS REFERENCE TO RELATED APPLICATION

This application relates to and claims priority on U.S. Provisional Application No. 60/118,779, filed Feb. 5, 1999, and 60/137,702, filed Jun. 7, 1999.

FIELD OF THE INVENTION

The present invention relates generally to a surgical guide line assembly. In particular, the present invention is directed to a surgical guide line assembly for use in remote controlled surgical procedures. The present invention also related to a separator assembly for use in connection with the surgical guide line assembly to ensure that surgical components do not become entwined during a surgical procedure.

BACKGROUND OF THE INVENTION

Recent developments in the repair of abdominal aortic aneurysms permit minimally invasive surgical procedures through either an axillary or brachial incision or both. This requires the remote manipulation of both a repair graft and surgical components.

OBJECTS OF THE INVENTION

It is an object of the present invention to provide a guide line assembly for use in intravascular surgical procedures.

It is another object of the present invention to provide a guide line assembly for use in the manipulation of a surgical component within a vessel during an intravascular surgical procedure.

It is another object of the present invention to provide a guide line assembly for use in the manipulation of a repair graft assembly within a vessel during a surgical procedure for repairing an aneurysm.

It is another object of the present invention to provide a guide line assembly having a simple construction.

It is another object of the present invention to provide a guide line assembly that can be releasably secured to a surgical component for manipulation of the component within a vessel during a surgical procedure.

It is another object of the present invention to provide a guide line assembly that is capable of being attached to a surgical component at least one location.

It is another object of the present invention to provide a guide line assembly having a flexible curved end portion.

It is another object of the present invention to provide a separator assembly for use during a surgical procedure to ensure that surgical components do not become entwined during a surgical procedure.

It is another object of the present invention to provide a separator assembly that is capable of manipulating a graft assembly within a vessel.

It is another object of the present invention to provide a separator assembly having a separating assembly that is capable of rotating within the vessel.

It is another object of the present invention to provide a separator assembly having a separating assembly that is capable of being selectively locked with the vessel.

SUMMARY OF THE INVENTION

The present invention is directed to a surgical guide line assembly for use during a surgical procedure. The surgical guide line assembly permits the manipulation of a surgical component within a vessel during a surgical procedure, such as for example an intravascular procedure. The surgical guide line assembly includes a guide line component having a proximal end and a distal end, and at least one suture secured to the distal end of the guide line component. The surgical guide line assembly may further include a surgical needle connected to each of the at least one suture. The surgical guide line according to the present invention may further include a broad line assembly that is positioned around the distal end of the guide line component and a portion of the at least one suture. The broad line assembly produces a flexible curved end portion of the guide line assembly.

The surgical guide line assembly may further include a control assembly connected to the guide line component The control assembly permits manipulation of the guide line assembly within the vessel from a remote location.

The present invention is also directed to a surgical guide line assembly for use during a surgical procedure. The surgical guide assembly permits the manipulation of a surgical component within a vessel during a surgical procedure, such as for example an intravascular procedure. The surgical guide line assembly includes a guide line component having a proximal end and a distal end, and at least one suture secured to the distal end of the guide line component. The surgical guide line assembly may further include a surgical needle connected to each of the at least one suture. The at least one suture according to the present invention may be secured to the guide line component in one of several ways. It may be bonded directly to the component The at least one suture may be secured to the guide line component within a formed cavity in the distal end of the guide line component. Alternatively, the suture may be secured to the distal end of the guide line component within a central passageway in the component.

In accordance with embodiments of the present invention, the guide line component may have a bent portion located adjacent the distal end. Alternatively, the guide line component may have an articulated portion located adjacent the distal end. The control assembly is capable of permitting manipulation of the articulated portion of the guide line component.

The present invention is also directed to a surgical separator assembly for use in separating at least two surgical components during a surgical procedure in a vessel. The surgical separator assembly includes a separating assembly for receiving the at least two surgical components during the surgical procedure. The surgical separator assembly further includes an advancing assembly for advancing the separating assembly within the vessel during the surgical procedure. The advancing assembly may include a catheter. The separating assembly may be rotatably connected to the advancing assembly. The separator assembly further includes a control assembly for selectively locking the separating assembly to prevent rotation of the separating assembly. In accordance with the present invention, the separating assembly may include at least two apertures therein. Each of the apertures is sized to receive at least a portion of a surgical component therein.

The present invention is also directed to a surgical system for use during a surgical procedure within a vessel. The surgical system includes both the guide line assemblies described herein in combination with the surgical separator assembly.

It is to be understood that both the foregoing general description and the following detailed description are exemplary and explanatory only, and are not restrictive of the invention, as claimed. The accompanying drawings, which are incorporated herein by reference, and which constitute a part of this specification, illustrate certain embodiments of the invention, and together with the detailed description serve to explain the principles of the present invention.

BRIEF DESCRIPTION OF THE DRAWINGS

The invention will be described in conjunction with the following drawing in which like reference numerals designate like elements and wherein.

DETAILED DESCRIPTION OF PREFERRED EMBODIMENTS

Figure 2:
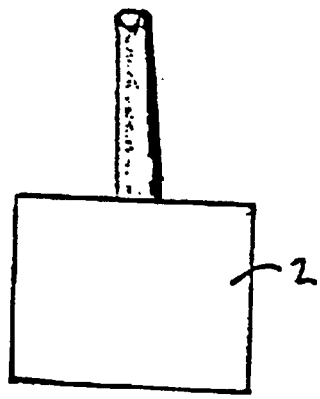
FIG. 2 is a schematic view of the guide line assembly according to FIG. 1 secured to a repair graft.
Figure 2:
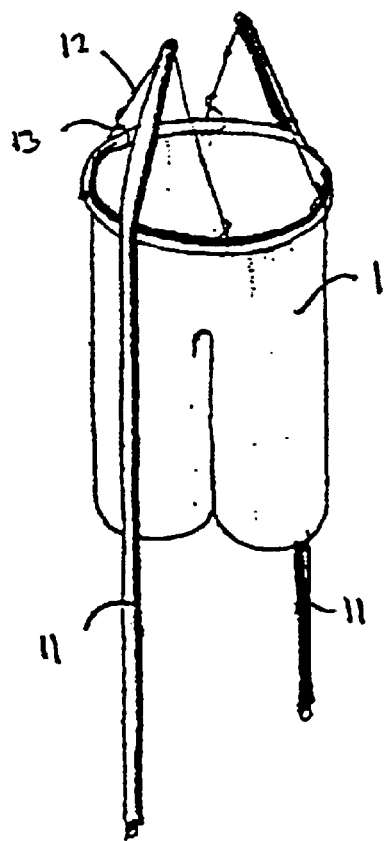

The above-described figures depict various surgical guide line assemblies according to embodiments of the present invention. These guide line assemblies are adapted for use in connection with the surgical repair of an aneurysms, as described in copending U.S. patent application Ser. No. 09/121,706, entitled "SURGICAL CUTTING DEVICE" filed on Jul. 24, 1998, the disclosure of which is incorporated herein by reference. At least one guide line assembly may be used to align and manoeuvre a repair graft, disclosed in U.S. patent application Ser. No. 08/896,415, entitled "METHOD AND APPARATUS FOR THE SURGICAL REPAIR OF ANEURYSMS" filed on Jul. 18, 1997, now U.S. Pat. No. 5,944,750, specification of which is incorporated herein by reference, within an infra, juxta or renal positioning. The guide line assemblies may be radially positioned about the perimeter of the proximal lip of the repair graft assembly and extend caudad to the femoral incision and thereafter to a hand controller 2, shown in FIG. 2. It is also contemplated that the guide line assemblies may extend cephalad to the axillary or brachial incision. The operation of the hand controller permits the manipulation of the at least one guide line assembly, which in turn adjusts the positioning of the repair graft assembly within the vessel during the surgical procedure.

Use of the various guide line assemblies disclosed herein according to the present invention is not limited to the repair of aneurysms. It is contemplated by the present inventors that the guide line assemblies disclosed herein according to the present invention may be used in connection with numerous intravascular procedures.

Figure 1:
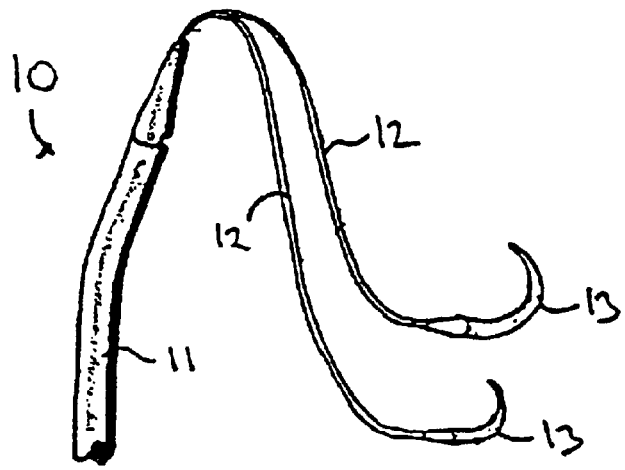
FIG. 1 is a perspective view of a guide line assembly according to an embodiment of the present invention.

The guide line assembly 10 according to an embodiment of the present invention, depicted in FIG. 1, will now be described in greater detail. Guide line assembly 10 includes a guideline component 11. The guide line component 11 has a distal end which is located within the vessel during the surgical procedure and a proximal end which extends from within the vessel. The guide line assembly 10 further includes at least one suture 12 connected to the guide line component 11. The at least one suture 12 is secured to one end of the guide line component 11. The guide line component 11 has sufficient length such that it may extend from within the vessel caudad to the femoral incision and thereafter to a hand controller 2. The guide line component 11 is preferably formed from nitonol. It, however, is contemplated that the guide line component 11 may be formed from a similar biocompatible material.

Figure 3:
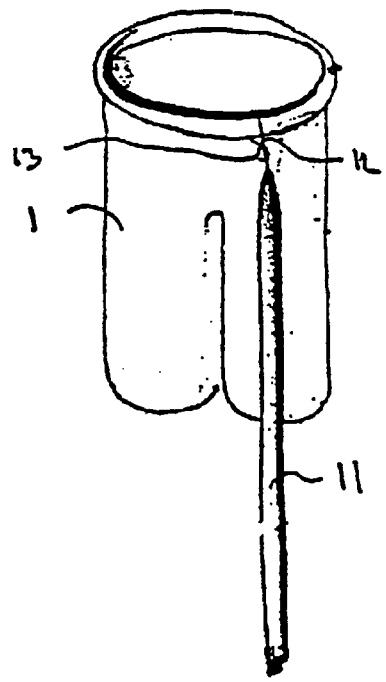
FIG. 3 is a schematic view of a guide line assembly according to another embodiment of the present invention secured to a repair graft.

At least one suture 12 is secured to the guide line component 11. The embodiment of the present invention illustrated in FIGS. 1 and 2 includes a pair of sutures 12. The present invention, however, is not limited to a pair of sutures 12. It is contemplated that a single suture 12 may be used as shown in FIG. 3. Furthermore, it is also contemplated that a plurality of sutures may extend from the distal end of the guide line component 11. The sutures 12 are mechanically coupled to the distal end of the guide line component 11. For example, the at least one suture 12 may be bonded to the end of the guide line component 11, as shown for example in FIG. 1.

Figure 8:
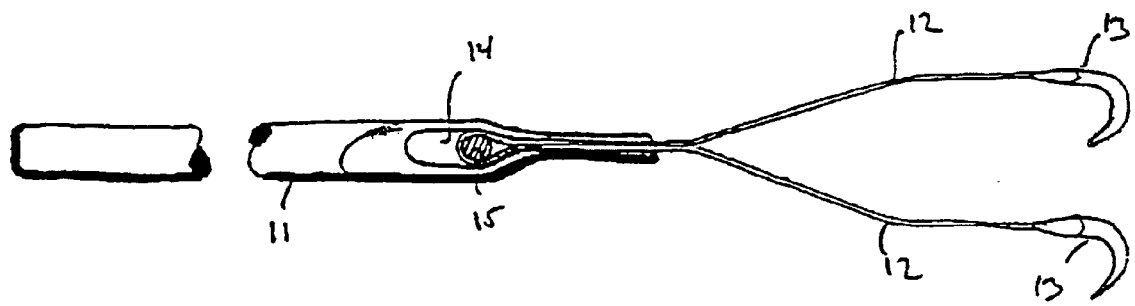
FIG. 8 is a partial cross section of a guide line assembly according to another embodiment of the present invention.
Figure 9:
FIG. 9 is a perspective view of the guide line assembly according to the embodiment of FIG. 8.

Other forms of coupling are considered to be well within the scope of the present invention. For example, another coupling attachment is illustrated in the embodiment depicted in FIG. 8. In this embodiment, the at least one suture 12 is crimped to the end of the guide line component 11. A formed cavity 14 is provided in the end portion of the guide line component 11. The at least one suture 12 is inserted into the formed cavity 14 such that the at least one suture 12 is held firmly in place upon crimping of the end of the guide line component 11. Additionally, an insert 15 may be provided within the cavity 14. The at least one suture 12 may be positioned around the insert 15 such that upon crimping of the end of the guide line component 11 the at least suture 12 is firmly secured to it. FIG. 9 is a perspective view of the end of the guide line component 11 in the crimped position.

Figure 10:
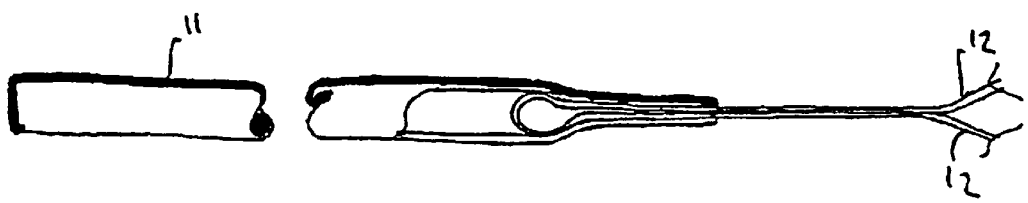
FIG. 10 is a perspective view of a guide line assembly according to another embodiment of the present invention.

FIG. 10 illustrates another embodiment of the coupling attachment for the guide line component 11. In this embodiment, the at least one suture 12 is crimped within the hollow portion, shown in FIGS. 4–7, of the guide line component 11. With this arrangement, no secondary drilling is required. In the embodiments illustrated in FIGS. 8–10, detailing of the transition between the guide line component 11 and the at least one suture 12 may be required to remove potential burrs as well as round the corners to prevent the unintentional separation of the guide line component 11 and the at least one suture 12. Furthermore, this detailing will prevent the guide line assembly 10 from becoming unintentionally caught within the vessel.

The guideline assembly 10 according to embodiments of the present invention includes a surgical needle assembly 13 secured to one end of the suture 12. The provision of the surgical needle assembly 13 facilitates the attachment of the guide line assembly 10 to a repair graft assembly 1, as shown for example in FIGS. 2 and 3.

Figure 4:
FIG. 4 is a cross section of the guide line component of FIGS. 1–3 according to one embodiment of the present invention.

The guide line component 11 may be formed in one of several profiles, as depicted in FIGS. 4–7. FIG. 4 illustrates a guide line component 11 according to the present invention having a rectangular profile 111 having rounded corners. The rounded corners facilitate smooth movement of the guide line assembly 10 within the vessel. The rectangular profile 111 may have a solid construction. A hollow or tubular construction having a central aperture 1110, shown in phantom, is also considered to be well within the scope of the present invention.

Figure 5:
FIG. 5 is a cross section of the guide line component of FIGS. 1–3 according to another embodiment of the present invention.

FIG. 5 illustrates a profile for the guide line component 11 according to another embodiment of the present invention. The guide line component 11 illustrated in FIG. 5 has an elongated or obround profile 112 having rounded ends. As discussed above in connection with the rounded corners, the rounded ends facilitate smooth movement of the guide line assembly 10 within the vessel. Additionally, the elongated profile 112 may have a solid construction. A hollow or tubular construction having a central aperture 1120, shown in phantom, is also considered to be well within the scope of the present invention.

Figure 6:
FIG. 6 is a cross section of the guide line component of FIGS. 1–3 according to another embodiment of the present invention.

FIG. 6 illustrates a profile for the guide line component 11 according to another embodiment of the present invention. The guide line component 11 illustrated in FIG. 6 has an elliptical profile 113. The elongated profile 113 may have a solid construction. A hollow or tubular construction having a central aperture 1130, shown in phantom, is also considered to be well within the scope of the present invention.

Figure 7:
FIG. 7 is a cross section of the guide line component of FIGS. 1–3 according to another embodiment of the present invention.

FIG. 7 illustrates a profile for the guide line component 11 according to yet another embodiment of the present invention. The guide line component 11 illustrated in FIG. 7 has a circular profile 114. The circular profile 114 may have a solid construction. A hollow or tubular construction having a central aperture 1140, shown in phantom, is also considered to be well within the scope of the present invention.

Figure 11:
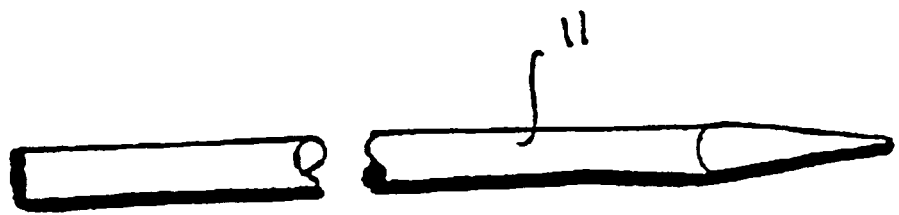
FIG. 11 is a perspective view of the end portion of the guide line component according to an embodiment of the present invention.
Figure 12:
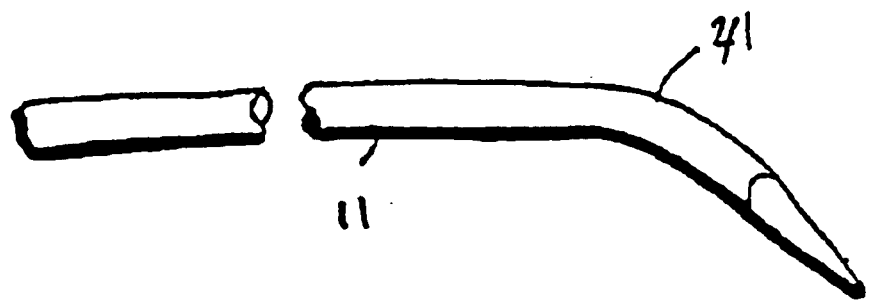
FIG. 12 is a perspective view of the end portion of the guide line component according to another embodiment of the present invention.
Figure 13:
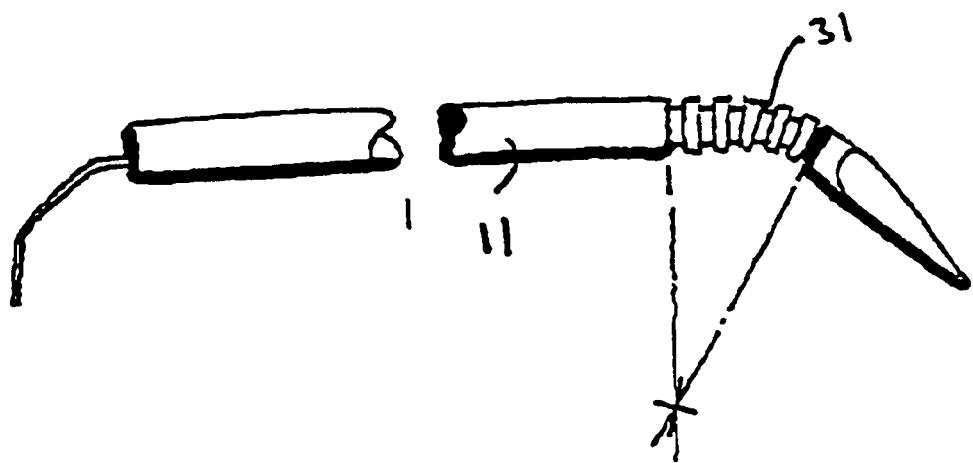
FIG. 13 is a perspective view of the end portion of the guide line component according to another embodiment of the present invention.

In accordance with embodiments of the present invention, the distal end of the guide line component 11 may have a linear orientation, as shown in FIG. 11. Alternatively, the distal end of the guide line component 11 may have a bent configuration 41, as shown in FIG. 12. The distal end of the guide line component 11 may be articulated to facilitate manipulation of the guide line assembly 10 within the vessel for positioning a surgical component such as for example a repair graft assembly 2, as shown in FIG. 13. In this embodiment, the guide line component 11 includes an articulated segment 31 located adjacent the distal end. The articulated segment 31 may be manually adjusted by the surgeon. It, however, is contemplated that the articulated segment 31 may be remotely adjusted using the hand controller 2 or other suitable manipulation assembly.

The operation of the guide line assembly 10 will now be described in connection with a repair graft assembly 2. It, however, is contemplated by the inventors of the present invention that the guide line assembly 10 may be used with other surgical components for use in other intravascular procedures. The guide line assembly 10 is secured to the repair graft assembly 2. Specifically, the surgical needle 13 is inserted through the lip of the repair graft assembly 2. The surgical needle 13 is then looped around the suture 12 to secure the guide line assembly 10 to the repair graft assembly 2. The surgical needle 13 is then removed. The repair graft 2 can then be inserted and maneuvered within the vessel. The positioning of the repair graft 2 within the vessel can be adjusted using the hand controller 2.

Figure 14:
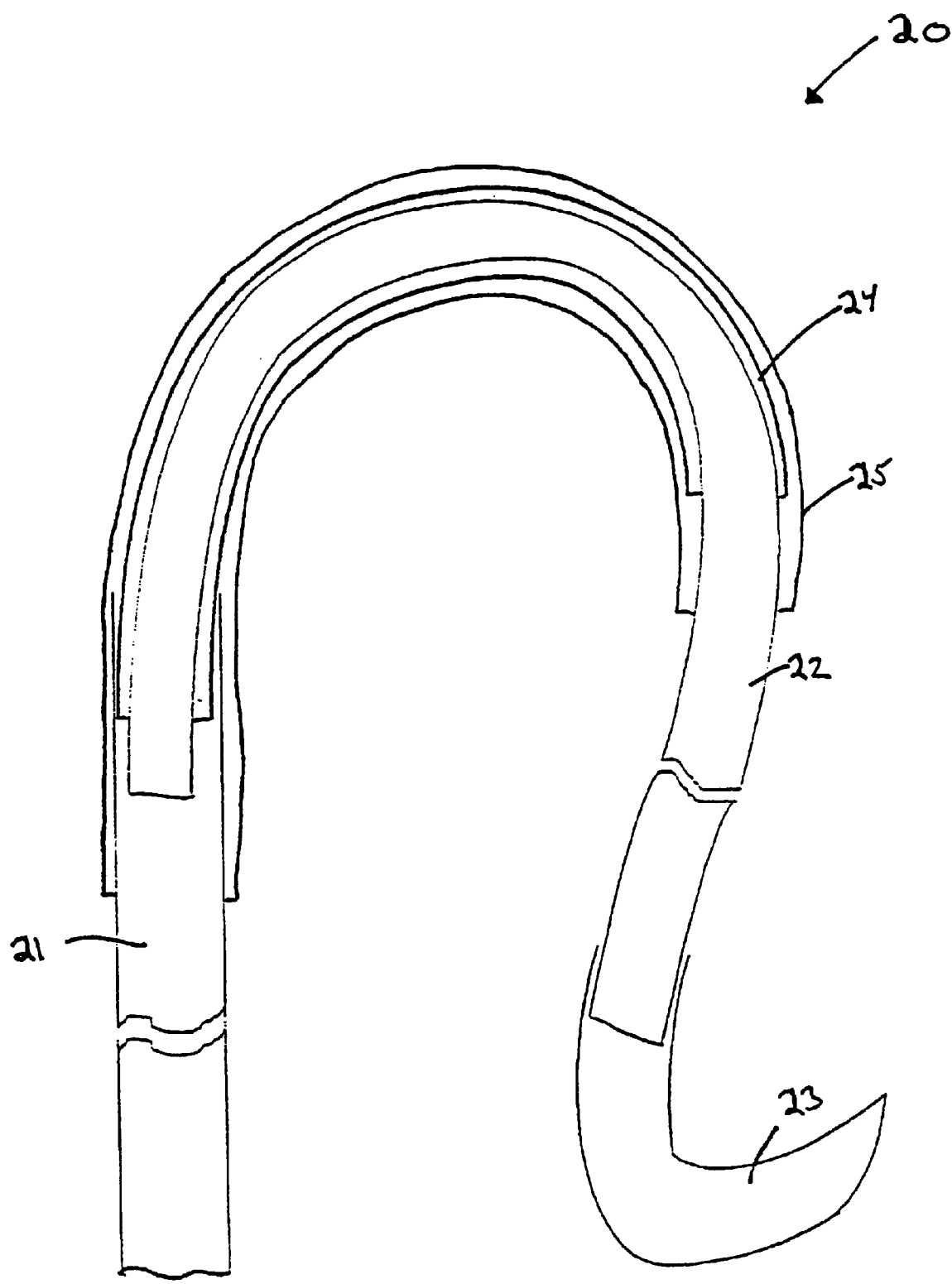
FIG. 14 is a perspective view of a guide line assembly according to another embodiment of the present invention.

The guide line assembly 20 according to another embodiment of the present invention, depicted in FIG. 14, will now be described in greater detail. Guide line assembly 20 includes a guide line component 21. The guide line component 21 is fairly stiff. The guide line component 21 has a distal end which is located within the vessel during the surgical procedure and a proximal end which extends from within the vessel. The guide line assembly 20 is manipulated within the vessel adjacent the proximal end of the guide line component 21. The guide line assembly 20 further includes at least one suture 22 connected to the guide line component 21. The at least one suture 22 is secured to one end of the guide line component 21. The guide line component 21 has sufficient length such that it may extend from within the vessel caudad to the femoral incision and thereafter to a hand controller as shown in FIG. 1 in connection with guide line assembly 10. The guide line component 21 is preferably formed from nitonol. It, however, is contemplated that the guide line component 11 may be formed from a similar biocompatible material.

At least one suture 22 is secured to the guide line component 21. The embodiment of the present invention illustrated in FIG. 14 includes a pair of sutures 22. The present invention, however, is not limited to a single suture 22. It is contemplated that more than one suture 22 may be used. The suture 22 is mechanically coupled to the distal end of the guide line component 21. For example, the at least one suture 22 may be bonded and/or crimped to the end of the guide line component 21. Other forms of coupling, however, are considered to be well within the scope of the present invention. The guide line assembly 20 according to embodiments of the present invention includes a surgical needle assembly 23 secured to one end of the suture 22. The provision of the surgical needle assembly 23 facilitates the attachment of the guide line assembly 10 to a repair graft assembly 20 or other suitable surgical component within the vessel. The distal end of the guide line assembly 20 may be curved, as shown in FIG. 14. A broad line assembly 24 surrounds the suture 22 adjacent the distal end of the guide line component 21. The broad line assembly 24 permits the distal end of the guide line assembly 20 to retain its curved shape. The broad line assembly 24 is preferably flexible. It is preferably formed from a spring type material. The end of the guide line component 21 and the suture 22 may be coated and/or sheathed with a thin layer 25 of Gore-Tex® or other suitable material. The thin layer 25 prevents the curved end portion of the guide line assembly 20 from snagging when it is manipulated within the vessel and/or removed from the vessel.

Figure 15:
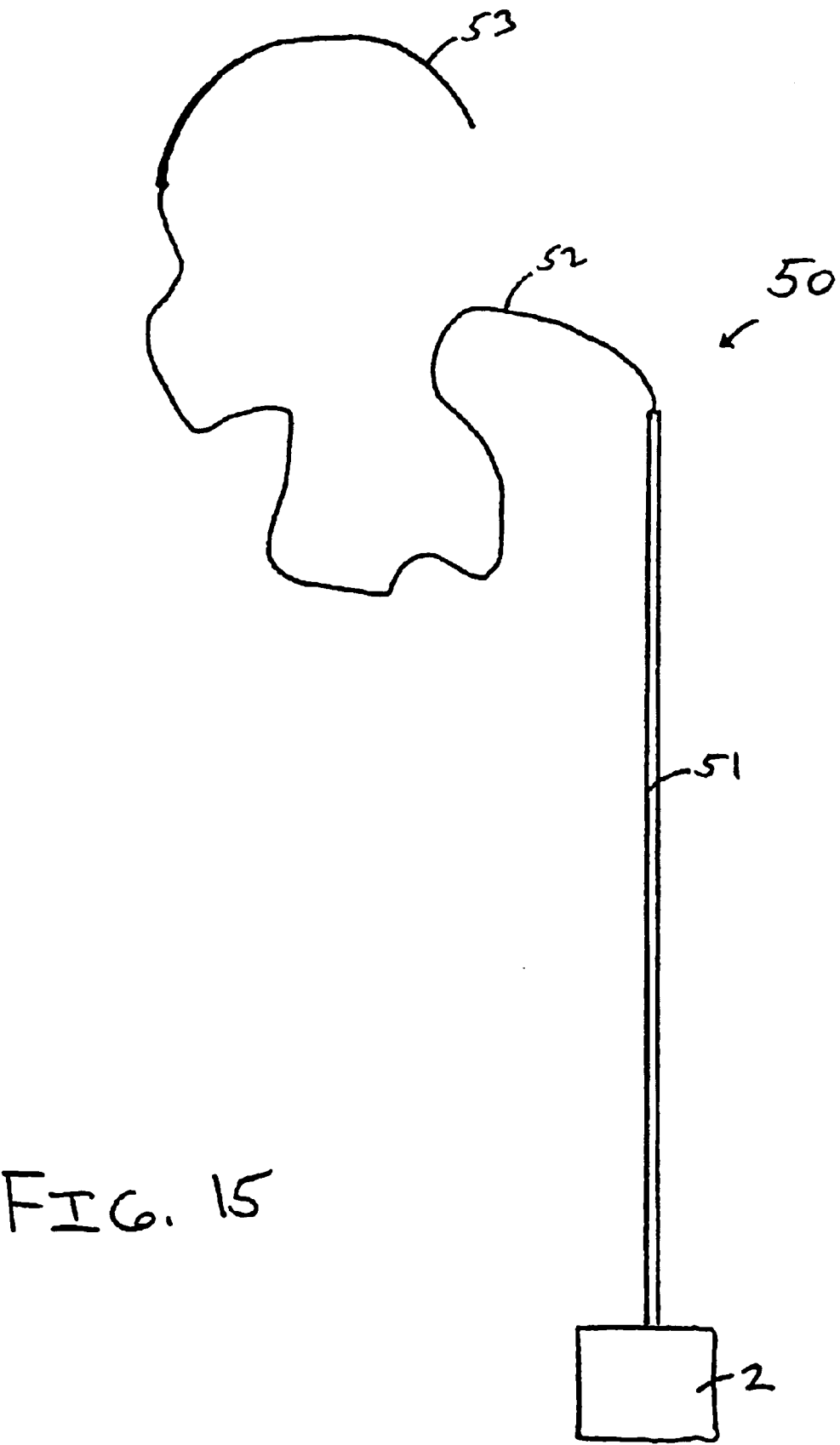
FIG. 15 is a perspective view of a guide line assembly according to another embodiment of the present invention.

A guide line assembly 50 according to another embodiment of the present invention is illustrated in FIG. 15. The guide line assembly 50 includes a guide line component 51, which is fairly stiff. The component 51 may be formed from a thin metal rod or needle. The component 51 has a distal end that is located within the vessel during the surgical procedure and a proximal end that extends from within the vessel. The guide line assembly 50 further includes at least one suture 52 secured to the distal end of the component 51. A surgical needle assembly 53 is secured to one end of the suture 52. The surgical needle assembly 53 may be straight or curved, as shown in FIG. 15.

Figures 16, 17:
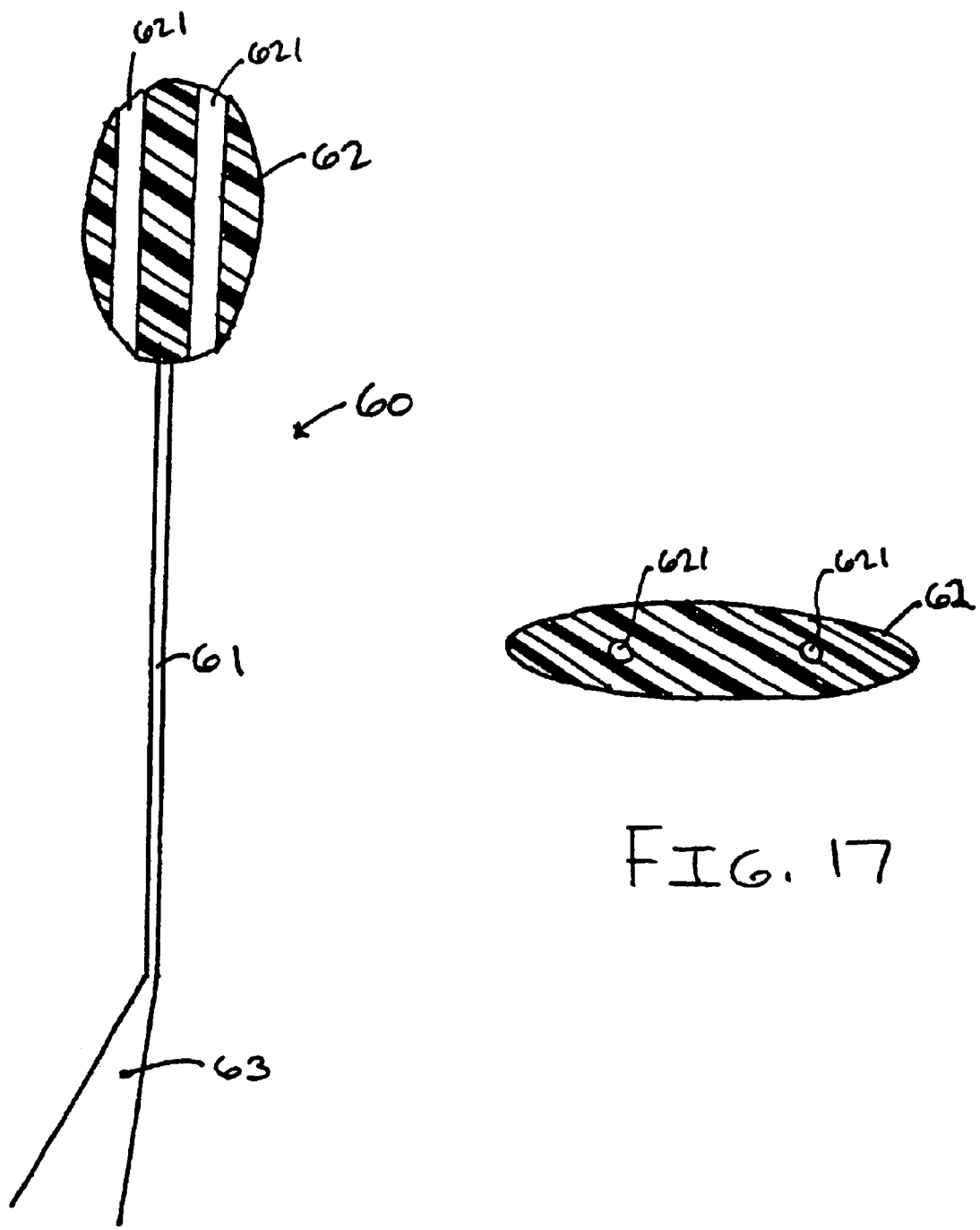
FIG. 16 is a perspective view of a guide line and suture separating assembly according to the present invention.
FIG. 17 is a cross section view of the head of the separating assembly of FIG. 16.

During a surgical procedure, it is possible that several guide line assemblies, described above, may be located within the vessel. It is possible that during the surgical procedure these guide line assemblies and sutures may become entwined, which may hamper the surgical procedure. Therefore, it is desirable to provide an assembly that is capable of separating any entwined guide line assemblies and sutures. A suture and guide line separator assembly 60 will now be described in connection with FIGS. 16 and 17. The separator assembly 60 includes a catheter assembly 61. One end of the catheter assembly 61 includes a separating assembly 62 connected thereto. The separating assembly 62 is capable of rotating about the axis of the catheter assembly 61. The separating assembly 62 includes a plurality of opening 621 are sized to receive a guide line assembly or a suture therein. An opposite end of the catheter assembly 61 includes a handle assembly 63. The handle assembly 63, when compressed, locks the separating assembly 62 in place such that it cannot rotate about the axis of the catheter assembly 61.

The operation of the separator assembly 60 will now be described. The free ends of the suture and guide line assemblies are threaded through the openings 621 in the separating assembly 62. The separator assembly 60 is advanced within the vessel along the sutures and guide line assemblies. The free ends of the sutures and the guide line assemblies located outside the vessel are preferably held in place to prevent insertion into the vessel while the separator assembly 60 is advanced to its furthest most position within the vessel. While the separator assembly 60 is advanced, the separating assembly 62 freely rotates about the catheter assembly 61. Once the separator assembly 60 reaches its furthest position within the vessel, the handle assembly 63 is operated to lock the separating assembly 62 to prevent its rotation. The separator assembly 60 may then be withdrawn from the vessel during which time the sutures and guide line assemblies may be straightened out and untangled. It is contemplated that the separator assembly 60 may be used in connection with any of the above described guide line assemblies. It is further contemplated that the separator assembly 60 may be used to separate sutures or a combination of sutures and guide line assemblies. It is further contemplated that the separator assembly 60 may be used in connection with any other surgical component that is capable of being entangled within a vessel during a surgical procedure.

Figure 18:
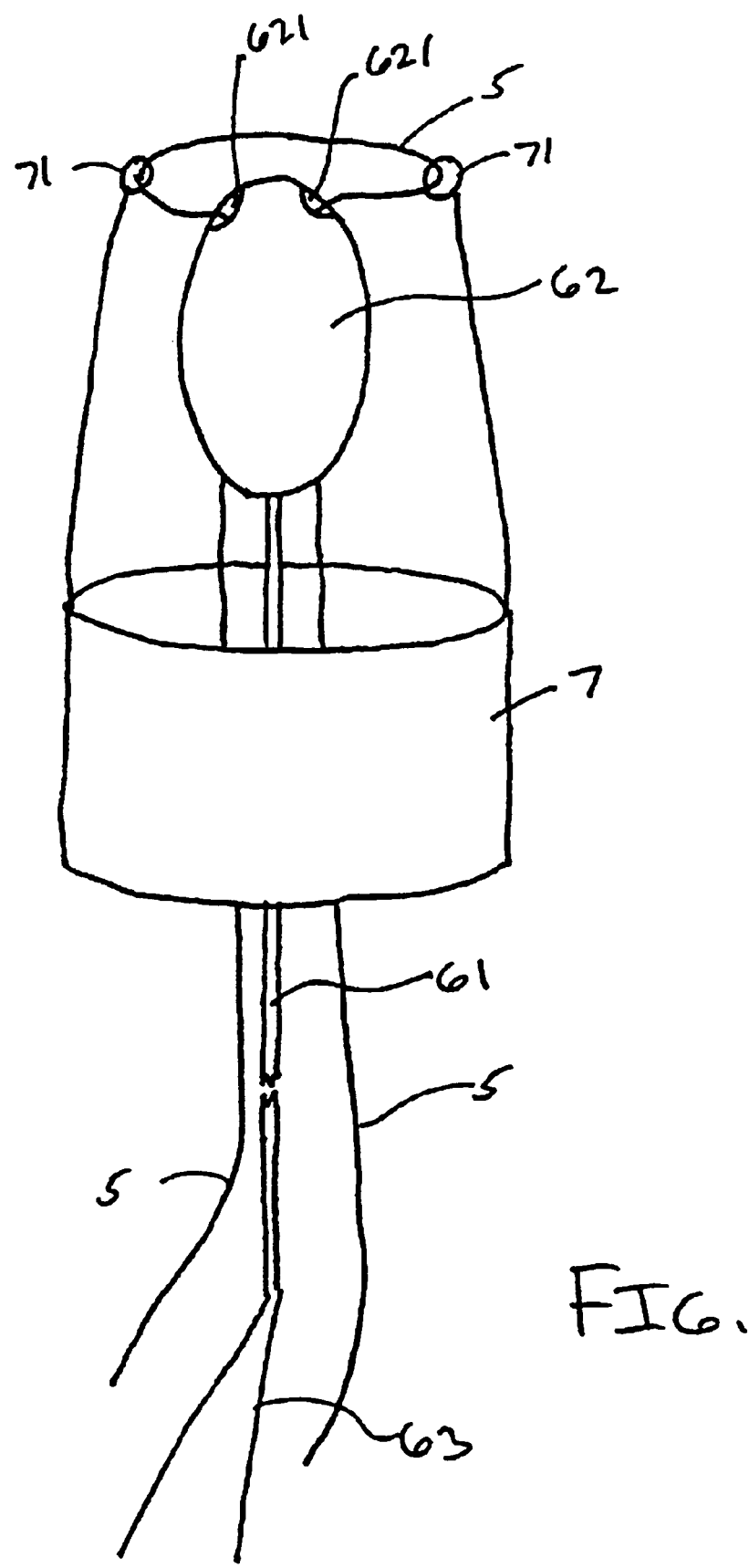
FIG. 18 is a schematic view of the separator assembly of FIG. 16 in accordance with the present invention used to position a graft assembly within a vessel.

It is further contemplated that the separator assembly 60 may be used to position and rotate a graft assembly 7 within the vessel, as shown in FIG. 18. A single suture 5 may be fed through two openings 621 in the separating assembly 62 and loops 71 on the graft assembly 7. The graft assembly 7 may be advanced into position within the vessel by inserting the separator assembly 60 into the vessel. As the separator assembly 60 is inserted, the graft assembly 7 and the separating assembly 62 will rotate freely about the axis of the catheter assembly 61. When the graft assembly 7 reaches the desired location, the handle assembly 63 is operated to prevent rotation of separating assembly 62. The catheter assembly 61 may then be rotated to position the graft assembly 7 in the desired location.

It will be apparent to those skilled in the arts that various modifications and variations can be made in the construction and configuration of the present invention, without departing from the scope or spirit of the invention. It is intended that the present invention cover the modifications and variations of the invention, provided they come within the scope of the appended claims and their equivalence.

What is claimed is:

1. A surgical guide line assembly for use during a surgical procedure, said surgical guide line assembly comprising:
   a repair graft assembly;
   a guide line component having a proximal end and a distal end; and
   at least one suture secured to said distal end of said guide line component and said repair graft assembly,
   wherein each of said at least one suture includes a first end secured to said distal end of said guide line component, and a second free end, said surgical guide line assembly further comprising:
   a surgical needle connected to said second end of said at least one suture,
   wherein said surgical needle facilitates the attachment of said guide line component to said repair graft assembly.

2. The surgical guide line assembly according to claim 1, further comprising:
   a control assembly connected to said guide line component, wherein said control assembly permits manipulation of said guide line assembly.

3. The surgical guide line assembly according to claim 1, wherein said guide line component has a bent portion located adjacent said distal end.

4. The surgical guide line assembly according to claim 1, wherein said guide line component has an articulated portion located adjacent said distal end.

5. The surgical guide line assembly according to claim 4, further comprising:
   a control assembly connected to said guide line component, wherein said control assembly enables manipulation of said guide line assembly.

6. The surgical guide line assembly according to claim 5, wherein said control assembly enables manipulation of said articulated portion of said guide line component.

7. The surgical guide line assembly according to claim 1, wherein said at least one suture is secured to said guide line component within a formed cavity in said distal end of said guide line component.

8. The surgical guide line assembly according to claim 1, wherein said guide line component has a central passageway extending therein, said at least one suture is secured to said distal end of said guide line component within said central passageway.

9. The surgical guide line assembly according to claim 1, wherein said at least one suture is bonded to said distal end of said guide line component.

10. A surgical guide line assembly for use during a surgical procedure, said surgical guide line assembly comprising:
    a repair graft assembly;
    a guide line component having a proximal end and a distal end;

at least one suture secured to the distal end of said guide line component and said repair graft assembly; and a broad line assembly positioned around said distal end of said guide line component and a portion of said at least one suture, wherein each of said at least one suture includes a first end secured to said distal end of said guide line component, and a second free end, said surgical guide line assembly further comprising:

a surgical needle connected to said second end of said at least one suture, wherein said surgical needle facilitates the attachment of said guide line component to said repair graft assembly.

11. The surgical guide line assembly according to claim 10, wherein said broad line assembly produces a flexible curved end portion of said guide line assembly.

12. The surgical guide line assembly according to claim 10, further comprising:

a thin layer of material positioned about said distal end of said guide line component and said at least one suture adjacent said broad line assembly.

13. The surgical guide line assembly according to claim 12, wherein said thin layer of material is formed from polytetrafluoroethylene.

14. A surgical guide line assembly for use during a surgical procedure, said surgical guide line assembly comprising:

a repair graft assembly;

a guide line component having a proximal end and a distal end; and at least one suture secured to said distal end of said guide line component and said repair graft assembly, wherein said at least one suture is secured to said guide line component within a formed cavity in said distal end of said guide line component.

15. A surgical guide line assembly for use during a surgical procedure, said surgical guide line assembly comprising:

a repair graft assembly;

a guide line component having a proximal end and a distal end; and at least one suture secured to said distal end of said guide line component and said repair graft assembly, wherein said guide line component has a central passageway extending therein, said at least one suture is secured to said distal end of said guide line component within said central passageway.

* * * * *